Figure 1:
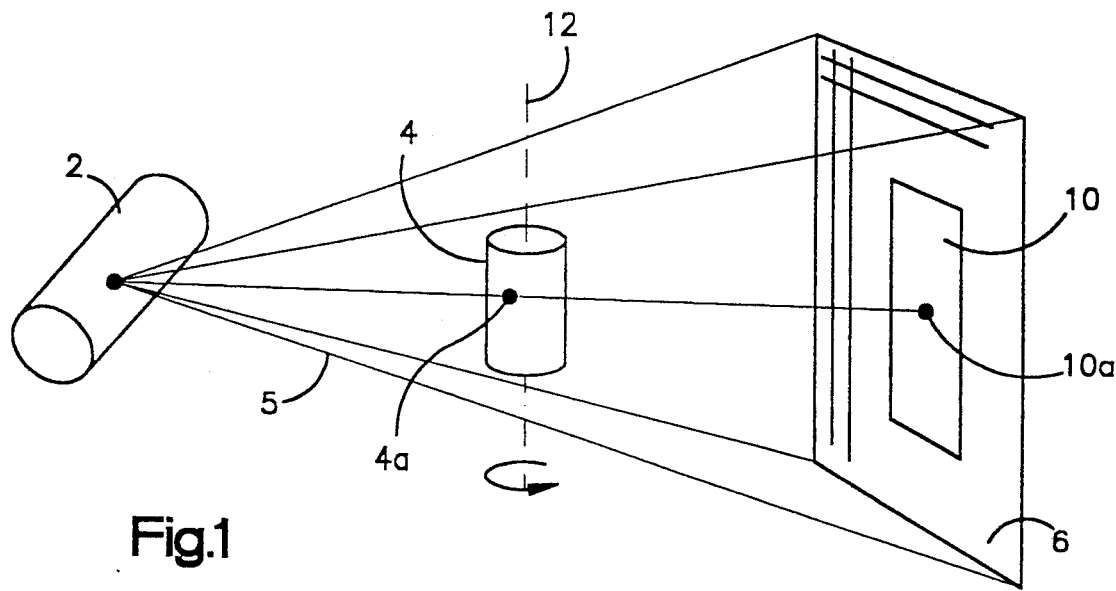

United States Patent [19]

Peyret et al.

[11] Patent Number: 5,164,971
[45] Date of Patent: Nov. 17, 1992

[54] NON-DESTRUCTIVE TESTING APPARATUS AND PROCESS WITH SIMULTANEOUS ACQUISITION OF RADIOGRAPHIC DATA AND TOMOGRAPHIC DATA

[75] Inventors: Olivier Peyret, Grenoble; Gérard Thomas, Pont de Claix, both of France

[73] Assignee: Commissariat a l'Energie Atomique, Paris, France

[21] Appl. No.: 781,015

[22] Filed: Oct. 18, 1991

[30] Foreign Application Priority Data

Nov. 5, 1990 [FR] France .................... 90 13660

[51] Int. Cl.⁵ .................................. A61B 6/03
[52] U.S. Cl. ................................ 378/4; 378/8; 378/19; 378/901
[58] Field of Search ............. 378/4, 8, 15, 17, 19, 378/20, 901, 21, 22, 23

[56] References Cited

U.S. PATENT DOCUMENTS

| 4,852,131 | 7/1989 | Armistead | 378/4 |
| 5,023,895 | 6/1991 | McCroskey et al. | 378/4 |
| 5,068,882 | 11/1991 | Eberhard | 378/4 |
| 5,073,910 | 12/1991 | Eberhard et al. | 378/4 |

FOREIGN PATENT DOCUMENTS 0176314 4/1986 European Pat. Off. .
0292402 11/1988 European Pat. Off. .
0365979 5/1990 European Pat. Off. .
2169180 7/1986 United Kingdom .

OTHER PUBLICATIONS

Patent Abstract-Industrial CT Scanner-Japan-6-1-28850(A)-Feb. 8, 1986.

Primary Examiner—David P. Porta
Attorney, Agent, or Firm—Pearne, Gordon, McCoy & Granger

[57] ABSTRACT

Non-destructive testing apparatus and process with the simultaneous acquisition of radiographic data and tomographic data comprises a gamma or X-ray source-detector assembly (2-6), an object support (16) placed between the source and the detector, means (17) for ensuring at least one relative rotary movement of the support with respect to the source-detector assembly, the detector being a bidimensional detector supplying for each point of each radiographic projection an analog signal proportional to the radiation quantity transmitted by the object (4), an analog-digital converter (21) for converting the signals from the detector into digital data, a first memory (28) for storing said digital data, a system (30) for the extraction and accumulation of part of said stored data, corresponding to at least one particular zone of the object to be tested or examined, a second memory (32) for storing the sinograms obtained from the selected and accumulated data and a system for processing these sinograms in order to reconstruct the tomographic sections.

9 Claims, 5 Drawing Sheets

NON-DESTRUCTIVE TESTING APPARATUS AND PROCESS WITH SIMULTANEOUS ACQUISITION OF RADIOGRAPHIC DATA AND TOMOGRAPHIC DATA

DESCRIPTION

The present invention relates to a non-destructive testing, inspection or examination apparatus and process with simultaneous acquisition of radiographic data and tomographic data. This apparatus can be used for industrial or medical applications. It utilizes radiographic methods (X or gamma rays) and makes it possible to analyze the internal structure of objects having variable dimensions and weights and in particular makes it possible to detect and analyze any faults, defects or errors. It can function in a wide radiation energy range and in particular from 1 KeV to 25 MeV, which covers that conventionally used in medical radiography or tomography.

Among these methods, the present invention is more particularly interested in those making it possible to acquire directly digitized radiograms (digital radiography). The invention more particularly applies to the car, aeronautic, space and nuclear sectors.

Any known digital radiography apparatus comprises a gamma or X-radiation source and a radiation detector associated with an acquisition electronics and an analog-digital conversion of the detected image. A data processing system then ensures the control (storage, processing, accumulation and display) of the digital images.

Figure 2:
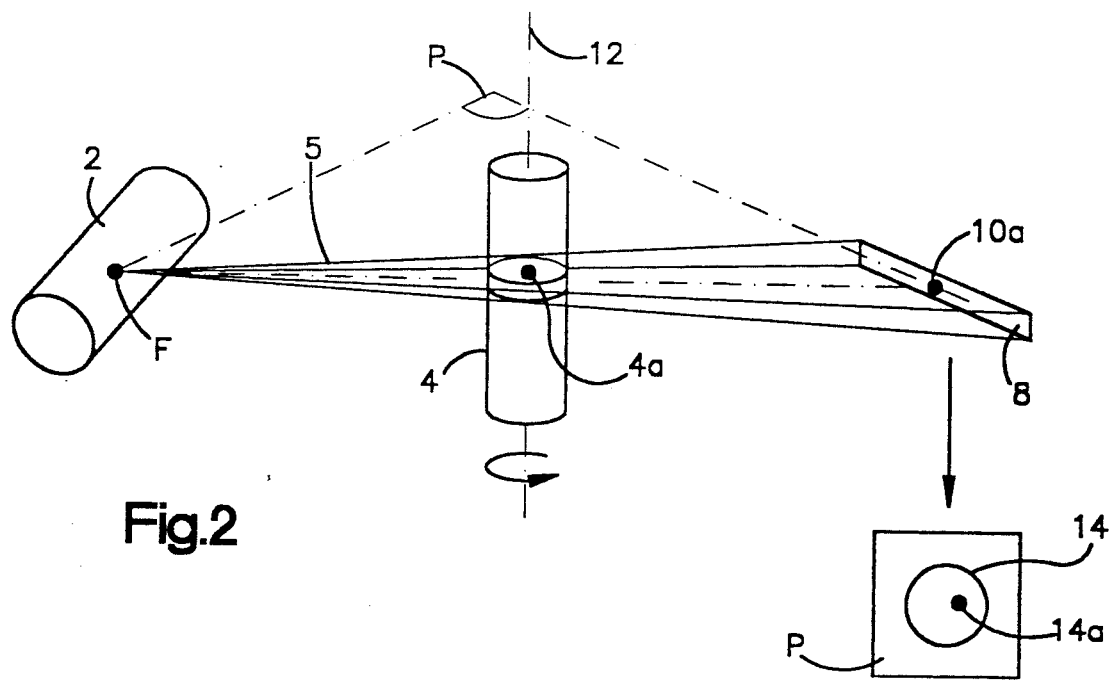

In known manner, the object to be radiographed is placed between the source and the detector, so that as a function of the apparatus used, it is possible to obtain at least two types of images, a radiographic projection like that shown in FIG. 1 and a tomographic section like that shown in FIG. 2.

In FIGS. 1 and 2, the references 2 and 4 respectively designate the radiation source (X or gamma) and the object to be radiographed. The reference 4a indicates a fault in the object and the reference 5 the radiation from the source. In the apparatus of FIG. 2, said radiation is collimated. The references 6 and 7 respectively represent a bidirectional detector with n rows and p columns and therefore a matrix of np detector points, called a 2D detector and a linear detector with 1 row and p points, called a 1D detector, n and p being natural integers exceeding 2 and generally between a few dozen and a few thousand.

In radiographic projection (FIG. 1), the source-object-detector assembly or unit is fixed and a radiogram 10 is obtained, which is a bidimensional representation of the transmission of the gamma or X-radiation through the object 4 and constitutes a conical projection of said object on the plane of the detector. Reference 10a represents the image of the object fault. This transmission image can be converted into an image representing at each point the attenuation of the gamma or X-radiation by the object.

By a rotation of the object or the source-detector assembly around the object, in accordance with an axis 12 transverse to the radiation 5, it is possible to acquire images of the object in accordance with different incidences, which can be necessary for its testing. An example of an operation functioning according to the principle of FIG. 1 is provided in FR-A-2 574 583 filed on Dec. 7, 1984 by the present Applicant.

In tomographic section (FIG. 2), there is a relative rotary movement along the axis 12 between the source-detector assembly and the object. A plane P perpendicular to the rotation axis 12 passing through the focus F of the source 2 and through the detector 8 is then defined and this is referred to as the section plane. During rotation, it is possible to acquire in said plane different series of measurements of the attenuation of the radiation by the object. These measurements are stored and used for the reconstruction, by means of a matched calculation algorithm, a tomographic view 14 of the object, which constitutes a cross-section of said object in the plane P. The reference 14a represents a section of the fault 4a. This section permits on the one hand a precise morphological study of the object and on the other density measurements at each point of the object in the case where the energy of the radiation is well adapted.

A certain number of tomographic apparatuses exist in the medical and industrial fields. In particular, reference is made to that of FR-A-2 512 533 filed on Sep. 10, 1981 in the name of the present Applicant and which is applied to the industrial sector.

More specifically, the invention relates to apparatuses making it possible to bring about a real time acquisition of directly digitized radiograms using a gamma or X-radiation (2D) bidimensional detector.

Among these 2D detectors, reference is made in non-limitative manner to:

radiogram intensifier tubes (or brightness amplifiers) associated with a video camera;

optically stimulatable radioluminescent screens, which are read by a laser beam, the signal from the screens being received on a photomultiplier (FUJI process);

radioluminescent screens associated with an image retaking optics and with a low light level camera.

Several published documents describe the latter type of detector and are more particularly interested in improving the performance characteristics of the radioluminescent screen. Reference can more particularly be made to FR-A-2 463 420 of Aug. 14, 1979 describing the use of such a detector for the testing of reinforced concrete structures and proposing a special structure of the radioluminescent screen, as well as FR-A-2 412 855 of Dec. 22, 1978 and FR-A-2 574 583 of Dec. 7, 1984 proposing different processes for the production of such screens and describing apparatuses for performing these processes.

Up to now, for non-destructive testing purposes, a certain number of radiographic projections 10 of an object to be tested have been made in accordance with the process described relative to FIG. 1. When a fault 4a is detected in a given zone of the object, there is interest in carrying out a tomographic section of the object with a view to a better pin-pointing of said fault and a possible measurement of the density of the fault.

The object is then subject to further X or gamma irradiations in order to produce tomographic sections. This leads to an increase in the time taken for non-destructive testing, which is disadvantageous for industrial production rates and requires the use of two separate apparatus types, which causes dimensional problems and makes it more difficult to handle the objects to be tested. In addition, this leads to high testing costs.

Moreover, when the object to be tested or examined is a human being, it is desirable to reduce to the greatest possible extent the irradiation time.

In order to decrease the irradiation time, a complex solution exists. On the basis of bidimensional measurements of the attenuation of the radiation by an object and specific algorithms, it consists of reconstructing the entire volume of the object and in this way produce a three-dimensional imaging apparatus. In particular, FR-A-2 615 619 of May 21, 1987 and deposited in the name of the Applicant describes such an apparatus using a specific algorithm.

On the basis of the reconstructed image of the volume, it is therefore obvious that with such a system, it is possible to extract any random plane having a section of the object and thus to have images of projections or sections of the object.

However, such a system involves complex data processing and electronics architecture, which is difficult to adapt to the industrial testing speed and cost requirements. Thus, the number of data to be processed in a reasonable period of time leads on the one hand to the use of a high performance computer and on the other hand to the production of reconstruction operators using a large number of processors (or parallel computers), whose cost is high.

In spite of this, the reconstruction times are long. Typically, for a volume of $128 \times 128 \times 128$ with 256 projections (128 being the number of points in a direction in space), an image of the volume is obtained in five hours on a VAX 6300 and in 15 minutes on a CRAY 2.

Moreover, for reconstructing the entire volume with the minimum of artefacts, it may be necessary to permit acquisitions with a complex relative movement of the source-detector assembly with respect to the object, which leads to a costly mechanical assembly.

The invention relates to a non-destructive testing apparatus and process with simultaneous acquisition of data of radiographic projections and data of tomographic sections making it possible to obviate the aforementioned disadvantages.

It permits in a simple, rapid and inexpensive manner to acquire radiographic data and tomographic data with the same apparatus. It also makes it possible to reduce the exposure time of the object to be tested to ionizing radiation. It can be used both in the industrial and in the medical field.

The present invention is based on the possibility of extracting during acquisition or with a time lag, data of a limited, but adequate number of radiographic projections of the object and to accumulate, optionally complete and structure these data in order to constitute a sinogram of a tomographic acquisition necessary for the reconstruction of a section of said object.

The invention also relates to a non-destructive testing apparatus with simultaneous acquisition of radiographic projection data of an object, and tomographic section data of said object, comprising an ionizing radiation source-detector assembly, an object support placed between the source and the detector, means for ensuring at least one relative rotary movement of the support with respect to the source-detector assembly, the detector being a bidimensional detector with several rows and several columns, supplying for each point of each radiographic projection an analog signal proportional to the radiation quantity transmitted by the object, an analog-digital converter for converting the signals supplied by the detector into digital data, a first memory for storing said digital data, an extraction and accumulation system of part of the stored data, corresponding to at least one particular zone to be inspected of the object, a second memory for storing sinograms obtained from the data selected and accumulated by the extraction system and a processing system for the said sinograms in order to reconstruct tomographic sections.

The invention has the advantage of being performable with any existing real time acquisition system for digital images using a gamma or X-radiation 2D detector. Ionizing radiation is understood to mean X or gamma radiation.

A sinogram is a matrix of j rows and p columns (j.p points), in which j corresponds to the number of radiographic projections at successive rotation angles with a constant angular spacing and p corresponds to the number of points of a row of detectors.

In the case of a linear detector used in conventional tomography, each row of the sinogram corresponds to the information of the row of the detector for a given projection.

In the case of the invention using a 2D detector, each row of the sinogram corresponds to the information, for a given projection, of one or more accumulated rows (sum of the points of the same abscissa of said rows) of the detector.

The apparatus according to the invention is a general-purpose apparatus making it possible to carry out both radiographic projections and tomographic sections of the same object. On the basis of the same acquisition sequence, it permits the production of views in projection and sections of the same object.

The invention also makes it possible to produce tomographic sections by choosing, following data acquisition, the section plane and height. Thus, on the basis of the same acquisition sequence, it is possible to produce several tomographic sections of the object in different section planes or in the same section plane with different section heights and in particular for producing the best compromise between the spatial resolution and the signal-to-noise ratio appropriate for the visual display of a detail. The section height corresponds to the number of selected rows and the section plane is defined by the rank or order of the selected central row.

Finally, it limits the irradiation time of the object, because it uses the same data for both image types.

With the system according to the invention, it is possible to use different processes for the non-destructive testing of an object. In particular, it is possible to process information supplied by the detector in real time or in deferred time (time lag). Moreover, this original device can be used in the conventional radiographic mode (information acquisition, storage of one or more projection views by the processing circuit) or in the conventional tomographic mode (collimation of the radiation, information acquisition and formation of a sinogram from a large number of projections.)

In the latter case, the section height is advantageously brought about with the aid of a primary collimation of the radiation beam emitted by the source, limiting the object diffused radiation.

Moreover, the use of a 2D detector in the case of conventional tomography gives the possibility of correcting the object diffused radiation. Use is then made of adjacent rows to the rows defining the section. These adjacent rows only cover the radiation diffused by the object. More detailed information on the correction of diffused radiation is provided in FR-A-2 504 278 filed on Apr. 15, 1981 by the present Applicant.

According to an embodiment of the apparatus according to the invention, the processing system incorporates a computer for controlling the entire apparatus and for the construction of the tomographic sections. This computer in particular controls the different memories of the apparatus, as well as the extraction system. It can also process data from the detector in order to carry out corrections.

Advantageously, this computer controls a visual display apparatus for the radiographic projections and/or tomographic sections and an access system to said computer. This computer also ensures the rotation control of the object or the source-detector assembly.

This computer can be completely integrated into the apparatus according to the invention or can be constituted by a first computer, integrated into the apparatus for the control thereof, and by a second computer, which is external with respect to the apparatus (e.g. located in an auxiliary device such as a tomograph), permitting the reconstruction of tomographic sections.

The first memory of the apparatus can make it possible to store and accumulate successive frames of the same projection in order to improve the quality of each radiographic projection. This more particularly applies when the detector operates at the video rate. The display apparatus can make it possible to diaplay each radiographic projection during the acquisition thereof.

Preferably, a second collimation device is positioned facing the detector in order to serve as a mask for the radiation coming directly from the source. This is particularly the case when the object to bě tested is smaller than the detector.

Advantageously there are filing means for the radiographic projections and/or tomographic sections of the object. These means can consist of magnetic tapes, disks or floppy disks and are connected to the computer.

The invention also relates to a process for the non-destructive testing of an object with simultaneous acquisition of radiographic projection data and tomographic section data with respect to said object and utilizing the apparatus described hereinbefore. This process comprises:

a) subjecting said object to ionizing radiation under different incidences, the object having at least one relative rotary movement with respect to the source-detector assembly, each incidence corresponding to a projection, b) detecting the radiation transmitted by the object with the aid of a bidimensional detector having several rows and columns, supplying at each point analog signals proportional to the radiation quantity transmitted by the object, c) converting said analog signals into digital data, d) storing said digital data in a first memory, e) processing the digital data in order to produce radiographic projections of the object, f) selecting at least one particular zone of the object to be tested, g) extracting from the first memory the digital data corresponding to said zone and accumulating the same for each projection, h) producing the sinogram corresponding to said zone from data extracted and accumulated from the different projections and i) processing said sinogram in order to reconstruct the tomographic section of the object in the selected zone.

A selected zone is defined by the section plane and the section height.

The process according to the invention makes it possible to obtain the same number of sinograms and therefore tomographic sections as there are selected zones.

The precise order of the stages of the process is in particular a function of the selected operating mode for the apparatus (e.g. deferred or real time operation).

In particular, stage g consists of extracting from the first memory n' rows of the j radiographic projections, on either side of the row of said projections corresponding to the centre of said particular zone and accumulate the $2n'+1$ rows, column by column, in order to obtain j rows corresponding to the j projections and each forming one row of the sinogram.

The invention is described in greater detail hereinafter relative to non-limitative embodiments and the attached drawings, wherein show:

FIG. 1, already described, diagrammatically the operating principle of a radiographic projection testing apparatus according to the prior art.

FIG. 2, already described, diagrammatically the operating principle of a prior art tomographic section testing apparatus.

Figure 3:
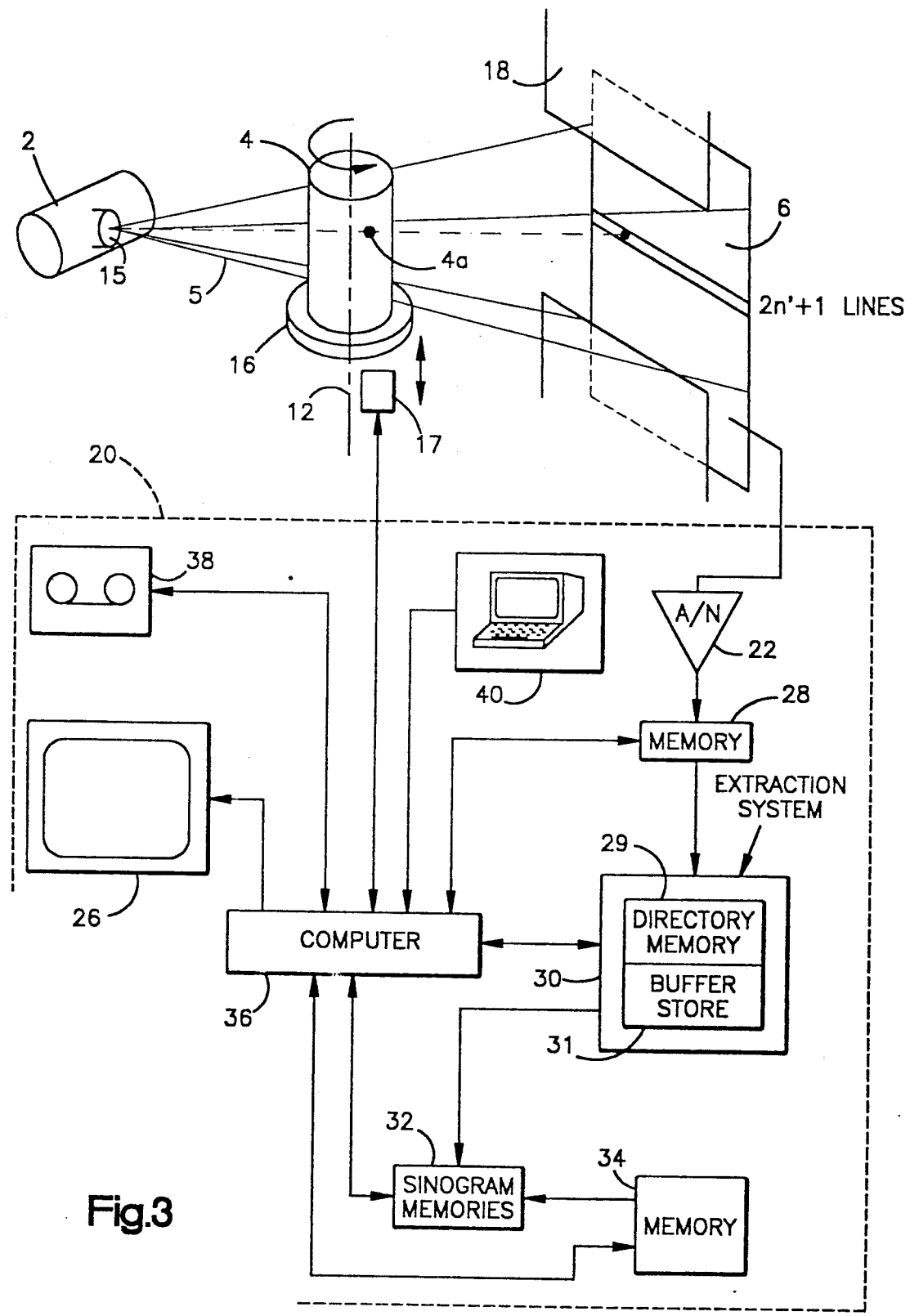

FIG. 3 A general mimic diagram of the testing apparatus according to the invention.

Figure 4:
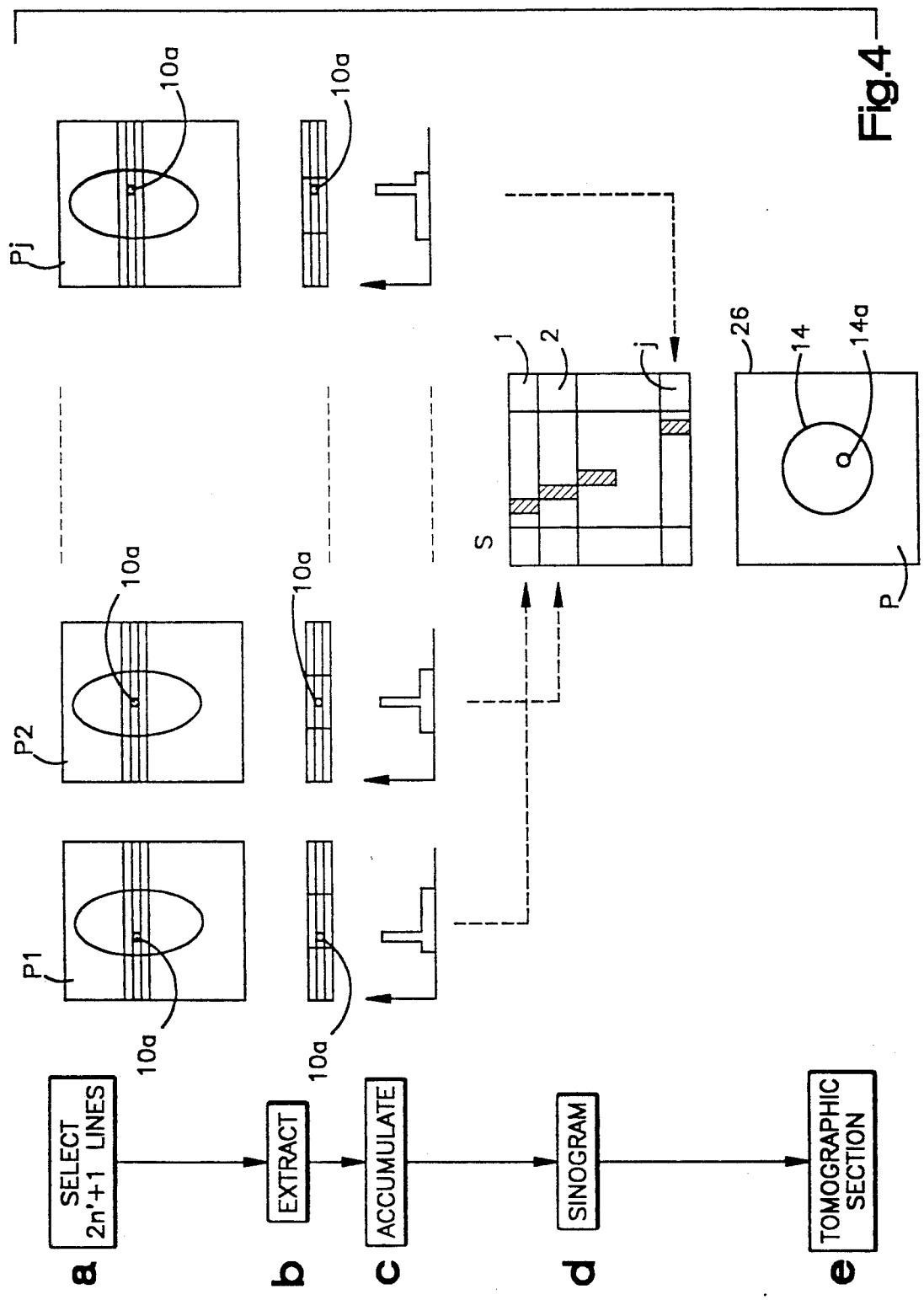

FIG. 4 The principle of the processing of information by the apparatus according to the invention.

Figure 5:
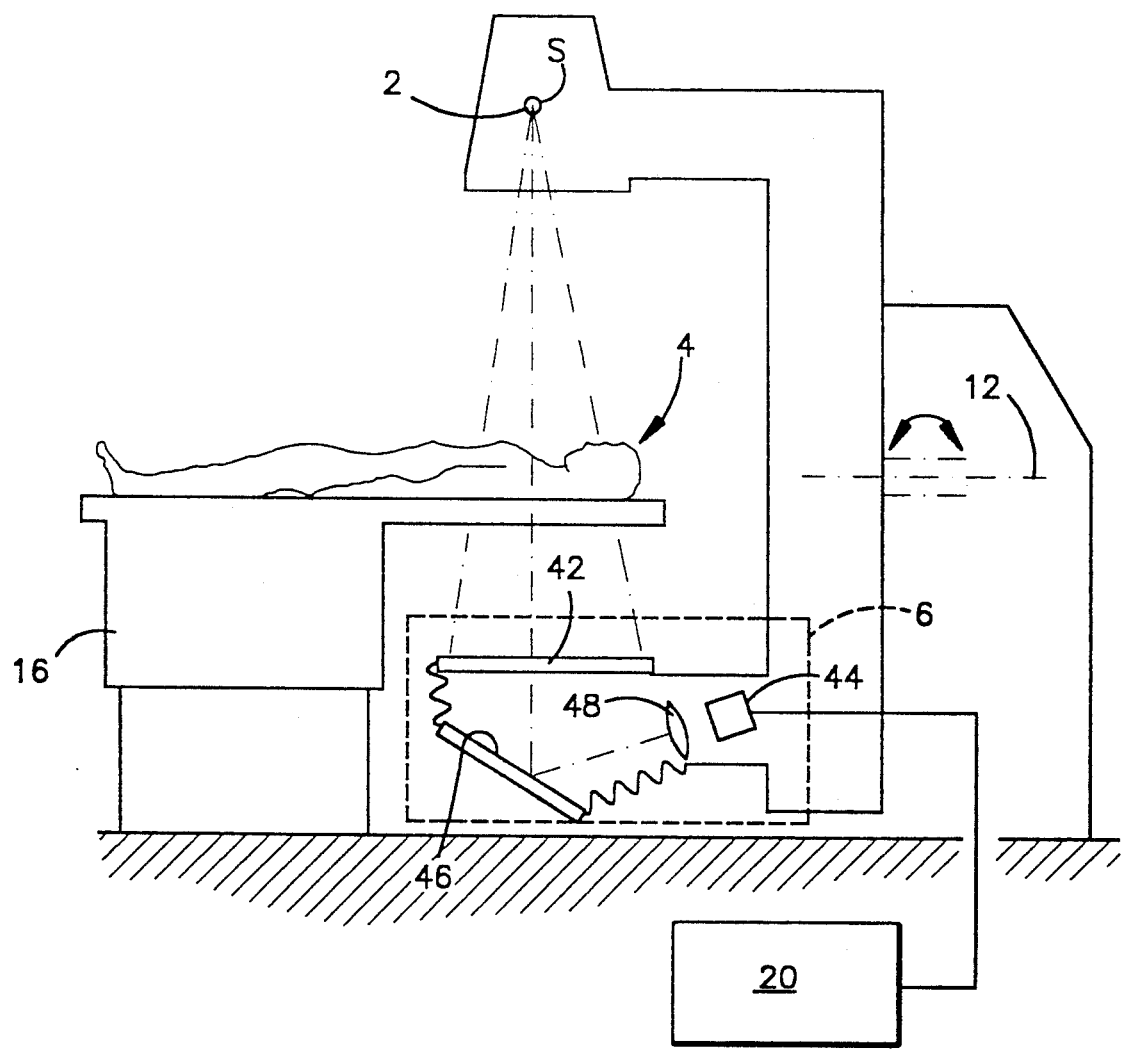

FIG. 5 An embodiment of the apparatus according to the invention for the medical field.

Figures 6A, 6B:
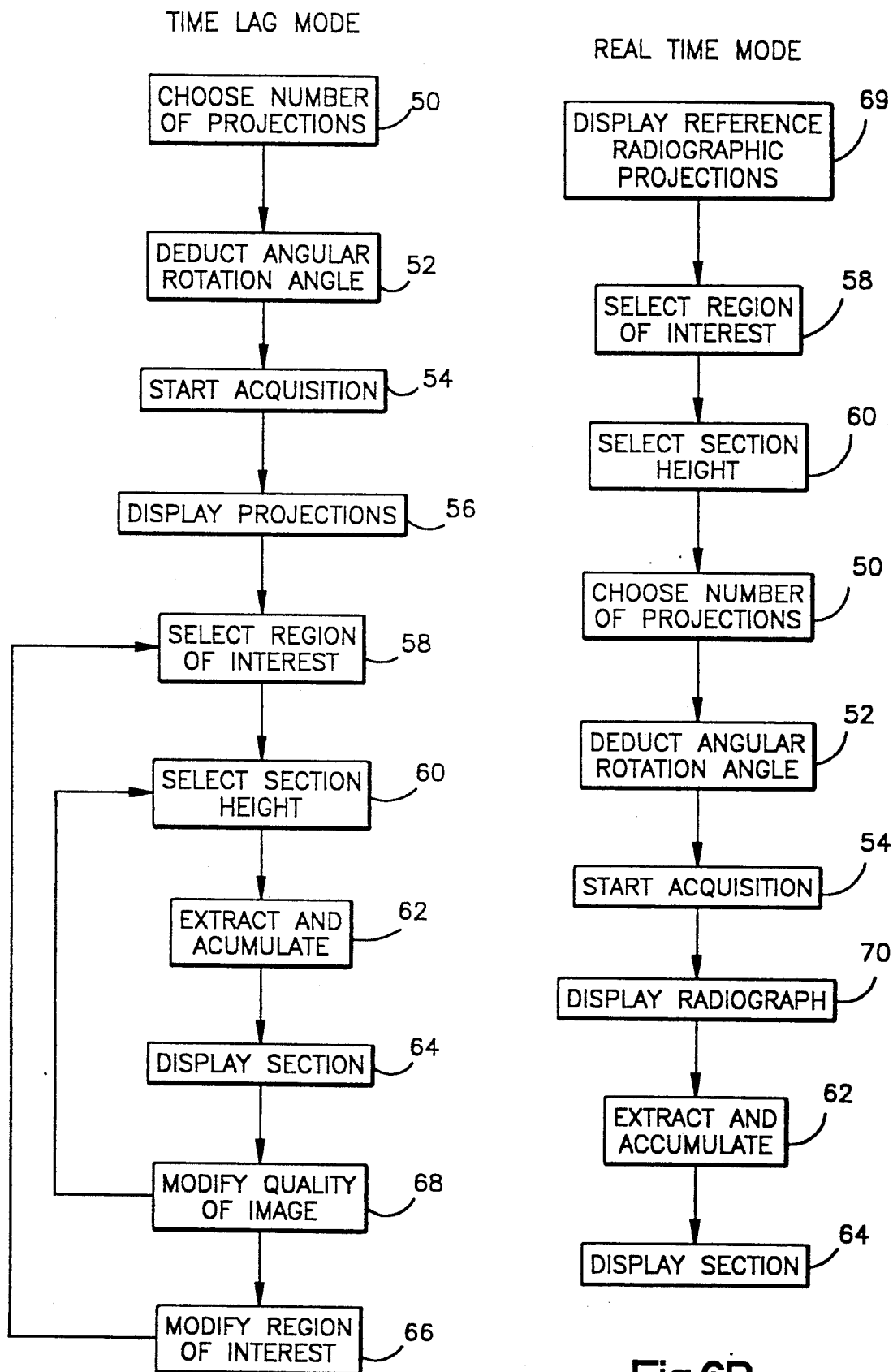

FIGS. 6A and 6B Mimic diagrams of the different operating stages of the apparatus according to the invention, respectively in the time lag mode and the real time mode.

With reference to FIGS. 3 to 5, the apparatus according to the invention comprises a gamma or X-radiation source as a function of the preferred energy range, such as an X-ray tube, a radioactive source or a linear accelerator. As a function of the apparatus, the X or gamma radiation energy can be adjustable. A primary collimator 15 (optional) can be placed at the outlet from the source in the case of use of conventional tomography.

The object to be radiographed 4 is linked with a mobile support 16, which is at least controlled in rotation along the axis 12 by a mechanical system 17. In a medical type application (FIG. 6), it is preferable if the rotary movement is produced by the source-detector assembly, the patient remaining stationary. The displacement system 17 can also e.g. permit a translation along the rotation axis.

A single radiographic projection corresponds to each orientation and position of the object relative to the source-detector assembly.

The bidimensional detection assembly 6 for the radiation measures the X or gamma radiation quantity at each point and supplies a matrix of analog data.

This detection assembly comprises n rows and p columns defining np image points (typically $512^2$ or $1024^2$ points). It permits the simultaneous acquisition of radiographic projection and tomographic section data. An example of a detector will be described hereinafter.

A secondary collimator 18 (optional), facing the detector 6, can be used as a mask for the direct radiation from the source 2, thus avoiding the saturation of the image points in question.

The aforementioned mechanical optical assembly is associated with an image processing system 20, connected at the detector output and which makes it possible to simultaneously produce radiographic projections and tomographic sections (FIG. 4). This assembly comprises an analog-digital converter 22 converting the analog signal supplied by the detector into digital data.

An image storage memory 28 makes it possible to record, during an acquisition sequence, a radiographic projection in the real time mode, or different radiographic projections P1, P2, ..., Pj in the deferred time or time lag mode (part a of FIG. 4) with j being an integer and ranging typically from 1 to a few hundred. Its capacity is calculated as a function of the maximum number of projections and the memory size of an image (number of points, coding).

This memory 28 makes it possible to accumulate a certain number of information frames, both in the real time mode and in the time lag mode during the acquisition of a radiographic projection in a given direction (this number of elementary images being defined by the operator), in order to increase the quality of the projections.

A visual display system 26 (e.g. monitor of the computer 36) makes it possible to display the information frames during acquisition (radioscopic mode) and the accumulated information frames, which consist of radiographic projections (radiographic mode). It also makes it possible to display in real time or time lag mode the tomographic sections.

The simultaneous display of radiographic projections and tomographic sections can be carried out on the same screen or on two screens.

An extraction and accumulation system 30 (software or specialized operator) makes it possible to rapidly extract (stage b, FIG. 4) from the different image planes P1, ..., Pj, the $2n'+1$ information rows selected by the operator for each zone of interest (with $2n'+1$ integer $\leq n$) in the image storage memory 28, either during the acquisition of the projections, the zone or zones of interest being defined by the operator or by the system prior to acquisition, or following the acquisition, the interest zone or zones then being defined by the operator after acquisition.

The extraction system 30 then carries out an accumulation (stage c, FIG. 4) of the $2n'+1$ selected information rows in each radiographic projection P1, P2, ..., Pj and for each interest zone (addition of the points of the same abscissa in each of the j projections).

Graph c in FIG. 4 is in fact a projection of the sinogram of part d of FIG. 4.

Thus, the extraction system constitutes all or part of the sinogram S by loading the sinogram memories 32. The latter can store data a priori on the radiographed object (stored beforehand in a memory 34) in order to enhance the sinogram. A computer 36 uses data from the memory 32 for reconstructing, with the aid of a matched algorithm, the desired tomographic section or sections (stage e, FIG. 4) displayed on the display screen 26.

The computer 36 also controls means 17 for the displacement of the object support and the control of the means 28, 29.

In the case where the computer 36 does not make it possible to reconstruct the tomographic sections, the memory 32 is constituted by a mobile support (disk, floppy disk, magnetic tape) making it possible to transfer data from the memory 32 to a tomograph computer positioned elsewhere and equipped with its own display system.

Magnetic tape-type filing means 38 can be associated with the apparatus, together with control means 40, such as a computer terminal.

The detector according to the invention can e.g. be constituted, in the manner shown in FIG. 5, by a terbium or europium-doped $Gd_2O_2S$ radioluminescent screen 42 associated with a video camera 44. In the medical application shown, the screen 42 is parallel to the support 16, which is in this case transparent to the radiation used and parallel to the ground. A flat mirror 46 can be provided for reflecting the light supplied by the screen 42 towards the intake of the camers after focussing with the aid of a lens 48. The mirror 46 is positioned at 45° from the perpendicular to the screen 42. The outlet of the camera is directly connected to the analog-digital converter 22.

A description will now be given of the operation of the apparatus according to the invention in the time lag mode (FIG. 6A) and then in the real time mode (FIG. 6B), in the case of an industrial application, where the object is rotated. The intervention of an operator is indicated by the hatching.

Time lag mode: preferably applied in an expertise logic

The user firstly determines (stage 50) the number j of radiographic projections to be carried out, the computer automatically deducting from j (stage 52) the angular rotation angle of the object 4 about the axis 12.

The object to be tested is then rotated and the user starts the acquisition of several object projection views. The rotating of the object coincides with the start of acquisition (stage 54). The operator then carries out a display of the projections during acquisition (radioscopic display) or after acquisition (radiographic display) (stage 56) on the display 26, in order to detect any fault or defect 4a.

A minimum number (j) of projections having been performed and these projections having been stored in the memory 28, the user carries out a tomographic section in the particular zone where the fault has been detected. The user then defines (stage 58) a region around the detected fault (e.g. order of the central row of the fault) and then defines (stage 60) a section height ($2n'+1$ rows, i.e. $n'$ selected rows on either side of said central reference row), as a function of the desired performance characteristics (spatial resolution, signal-to-noise ratio).

If the geometrical conditions (e.g. source remote from the detector with limited magnification or small body to be studied, etc.) of the apparatus are such that the divergence of the radiation beam is limited (parallel projection approximation), the defined region can be remote from the median plane (perpendicular to the rotation axis 12 and passing through the source).

The $2n'+1$ information rows chosen are extracted from each projection and accumulated point by point for each projection (stage 62) with the aid of the extraction and accumulation system 30. Each accumulated information row is stored in the memory 32 in order to constitute the sinogram S of a tomographic acquisition.

With the aid of a conventional reconstruction algorithm, the computer 36 then produces the section of the object (stage 64) in the defined plane P (or section plane). A tomographic reconstruction algorithm usable in the invention is e.g. that described in the book entitled "Actualité en Radiodiagnostic", subtitle "Nouvelles Technologies", by M. AMIEL et al, publisher MASSON, 1982, chapter 3 (New Tomographies), pp 26 to 28.

The user can define, for the same series of projections, several interest regions and thus carry out several tomographic sections in different planes. He can therefore modify the interest region (stage 66) (modification of the section plane) as well as the quality of each image (stage 68) (section height modification).

Real time mode: preferably applied in an automatic testing logic

The object to be tested has one or several specific zones for which it is a priori of interest to make a tomographic section (particular interest zone, complex geometry zone, pin-pointing a detail, etc.). Prior to testing, the user displays (stage 69) reference radiographic projections (earlier radiogram stored e.g. on the tape 38) on the monitor 26 and selects (stage 58) the interest zone or zones. The user can then define a zone a priori in the image and a section height (stage 60) in the same way as previously.

After fixing the section height, the user fixes the number of projections (stage 50) and then the computer deduces therefrom the angular spacing of the rotation of the object (stage 52) and then the user initiates the acquisition (stage 54).

It is possible to carry out on the monitor (stage 70) a radiographic display inspection of the rotating object, but in this mode the complete projections may not be retained beyond said display. Only the parts of said projections which are of interest are stored.

Only the information rows relating to the defined interest zone are extracted and accumulated with the aid of the system 30 and are then stored (stage 62) in the memory 32 in order to form in real time the tomographic acquisition sinogram. At the end of acquisition, the data are immediately available for the reconstruction of the tomographic section (stage 64) by means of the computer 36 and for display on the monitor 26.

In these two modes, in the case where the number j of projections is small, it is possible to use known procedures for completing the data during the formation of the sinogram with a view to improving the quality of the tomographic sections. It is possible to refer in this connection to the work "Utilization of the classical reconstruction algorithm for incomplete data in X-ray", E. Tournier, Ph. Rizo and G. Thomas, ASNT Conference, Jul. 25-27 1989, Seattle.

Two examples of use of the invention will now be given.

1. In an expertise logic (time lag mode)

Acquisition of radiographic projections in accordance with different incidences in the time lag mode of the object to be tested.

Display of these projections.

Locating a fault or a detail to be tested.

Section plane/height selections.

Producing one or more tomographic sections from said data.

Display and analysis of the sections.

Optional.

The fault justifies a more precise analysis: passage to the conventional tomographic mode, collimation, section plane/height selections, new acquisition of a large number of projections, display and analysis of an optimized tomographic section.

2. In an automatic testing logic (real time mode)

The automatic testing of the parts can justify the production of one or more projections and one or more tomographic sections in a sensitive region of the object and which is previously known.

Selection of said region—section plane/height from reference projections (a standard part).

For each part: acquisition of radiographic projections in accordance with different incidences in the real time mode.

Automatic production of required tomographic sections.

Analysis of the radiographic projections and tomographic sections by the system.

As a function of the result of the analysis, acceptance or rejection of the part.

Choice of the section plane

The section plane is defined a posteriori in the case of use of the time lag mode. The use of a 2D detector gives the possibility of at least 2 object rotation axes, as a function of the geometrical conditions of the apparatus. Thus, it is possible to select either information columns or lines in the digital image and the process described on the basis of a selection of rows can be described in the same way on the basis of a selection of columns.

Moreover, in the case where the divergence of the gamma or X-radiation beam is not negligible and the selected zone is remote from the median plane (passing through the focus of the radiation source), it is at least possible to obtain a good estimate of the position of a possible fault in the volume, by using a reconstruction utilizing rows (of different rank as a function of the projection), where said fault appears.

Choice of the section height

The section height corresponds to the number of accumulated rows. In the time lag analysis mode, it is a posteriori defined as a function of the quality of the desired image and in particular as a function of the density resolution/spatial resolution compromise.

A small number of rows (the number of rows depending on the size of the sought fault) permits a high definition to the detriment of the signal-to-noise ratio. The accumulation of several rows permits a better signal-to-noise ratio to the detriment of the spatial resolution.

Choice of the energy of the radiation

Particular attention must be paid to the choice of the energy of the X or gamma radiation used. Thus, as a function of the object to be radiographed and the measurements to be carried out, the optimum energy may not be identical in the different operating modes. It is also possible to use a simple device having a monoenergy source, which performs a compromise between the different modes, or on the contrary to use a device having a polyenergy source with an appropriate choice of the energy as a function of the mode.

The following description provides a possible example of the production of an extraction and accumulation system 30 (or extractor). The extractor is constituted by at the very least two memories.

There is a descriptor or directory memory 29 in which are recorded the extraction parameters supplied by the operator, namely the mode of the extraction (real or deferred time), the number of projections, the number of selected interest zones, the rank of the central information rows pin-pointing the zones and the number of selected rows per zone.

There is also a buffer store 31 in which are accumulated the selected rows. It is constituted by a minimum of one row on which are accumulated the $2n'+1$ rows of each zone of interest for each projection. The capacity of this buffer store defines the speed of extraction (possibility of carrying out in parallel the accumulation of rows of several interest zones and in the deferred mode of several projections recorded in the image storage memory.

The sinogram memory (independent or not of the preceding memories) receives the accumulated rows and constitutes the sinograms by an adequate addressing of the rows. The sinograms can be completed by data e.g. relating to the shape, density of the object, etc. present a priori in the sinogram memory.

In the real time mode, the extractor is synchronized on the acquisition or irradiation by the computer 36, the data being directly recovered in the memory 28 at the acquisition rate. The buffer store is optionally structured in order to accumulate in parallel the rows corresponding to different interest zones. The transfer to the sinogram memory 32 takes place at the acquisition rate. At the end of the acquisition of the projections, the sinogram memory is loaded.

In the deferred time mode, the extractor 30 operates on its own rate, which is dependent on the capacity of the buffer store, the data being recovered in the image storage memory 28.

In one industrial application of the invention linked with nondestructive testing for aerospace applications, the X-radiation source is a linear accelerator with an energy of MeV, the object is cylindrical and contains fuel, the aim being to detect delaminations close to the envelope and bubbles or blisters in the volume, the object performs a rotary and translation movement in accordance with the rotation axis 12 in order to test the assembly and the X-radiation detector is formed, as in FIG. 5, by a radioluminescent screen 42 associated with a wide field image retaking optical system (mirror 46) and a low light level camera 44.

The deferred time mode is appropriate for this testing or inspection in order to permit a good pin-pointing and a measurement of the density of the faults detected during the radioscopic examination.

We claim:

1. Non-destructive testing apparatus with simultaneous acquisition of radiographic projection data for an object and tomographic section data for said object, comprising an ionizing radiation source-detector assembly (2-6), an object support (16) placed between the source and the detector, means (17) for ensuring at least one relative rotary movement of the support relative to the source-detector assembly, the detector being a bidimensional detector with several rows and several columns, supplying for each point of each radiographic projection (P1, ..., Pj) an analog signal proportional to the radiation quantity transmitted by the object (4), an analog-digital converter (22) for converting the signal supplied by the detector into digital data, a first memory (28) for storing said digital data, a system (30) for the extraction and accumulation of part of said stored data corresponding to at least one particular zone of the object to be tested, a second memory (32) for storing sinograms obtained from the data selected and accumulated by the extraction system and a processing system (36) for said sinograms for the construction of tomographic sections (14).

2. Apparatus according to claim 1, characterized in that the processing system incorporates a computer (36) for the control of the apparatus and the reconstruction of tomographic sections, controlling a display apparatus (26) for the radiographic projections (P1, ..., Pj) and/or tomographic sections (14) and an access system (40) to said computer.

3. Apparatus according to claim 1, characterized in that a first collimator (15) is provided at the outlet from the source for collimating the radiation (5) from said source for carrying out conventional tomography.

4. Apparatus according to claim 1, characterized in that a second collimator (18) is provided facing the detector in order to serve as a mask for the radiation directly coming from the source.

5. Apparatus according to claim 1, characterized in that there are filing means (38) for the radiographic projections and/or tomographic sections of the object.

6. Apparatus according to claim 1, characterized in that the extraction system (30) incorporates at least two memories, a memory (29) in which are recorded extraction parameters of said part of the data and a memory (31) in which are accumulated the selected rows or columns.

7. Process for the non-destructive testing of an object comprising:
a) subjecting said object (4) to ionizing radiation (5) under different incidences, the object having at least one relative rotary movement with respect to the source-detector assembly, each incidence corresponding to a projection,
b) detecting the radiation transmitted by the object with the aid of a bidimensional detector (6) having several rows and columns, supplying at each point analog signals proportional to the radiation quantity transmitted by the object,
c) converting (22) said analog signals into digital data,
d) storing said digital data in a first memory (24),
e) processing (36) the digital data in order to produce radiographic projections (P1, ..., Pj) of the object,
f) selecting at least one particular zone of the object to be tested,
g) extracting (30) from the first memory the digital data corresponding to said zone and accumulating the same for each projection,
h) producing (32) a sinogram corresponding to said zone from data extracted and accumulated from the different projections and
i) processing (36) said sinogram in order to reconstruct a tamographic section of the object (14) in the selected zone.

8. Process according to claim 7, characterized in that extraction takes place from the first memory of n' rows or columns of each radiographic projection on either side of the row or column of these projections corresponding to the centre of said particular zone and in that they are accumulated column by column or row by row in each projection.

9. Process according to claim 7, characterized in that on a display (26) are displayed the radiographic projections (P1, ..., Pj) and/or the tomographic sections (14).

* * * * *